Figure 1:
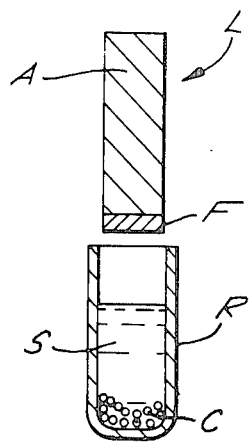

United States Patent [19]

Skare et al.

[11] 4,065,383

[45] Dec. 27, 1977

[54] PROCEDURE AND MEANS FOR COLLECTING LIQUID CONTAINING RADIOACTIVE TRACER ELEMENTS

[76] Inventors: Helge Skare, Heggtoppen, P.O. Box 8, 3401 Lierbyen, Norway; Henry Hirschberg, Studentbyen pa Kringsja, Sognsveien 218, Oslo 8, both of Norway

[21] Appl. No.: 672,679

[22] Filed: Apr. 1, 1976

[30] Foreign Application Priority Data

Apr. 14, 1975 Norway .................................. 751309

[51] Int. Cl.² ...................... B01D 15/00; B01D 35/00; G01N 33/16
[52] U.S. Cl. .................................... 210/27; 23/230 B; 23/230.3; 23/259; 23/292; 73/61 R; 73/425.4 R; 210/25; 210/359; 210/489; 210/DIG. 23; 250/303; 424/1.5
[58] Field of Search .................... 23/230.3, 230 B, 259, 23/292; 210/25, 359, 489, DIG. 23, 27; 73/61 R, 425.4 R; 250/303; 424/1.5

[56] References Cited

U.S. PATENT DOCUMENTS

| | | | |
|---|---|---|---|
| 2,672,431 | 3/1954 | Goetz | 73/61 R X |
| 3,380,888 | 4/1968 | Numerof et al. | 23/230 B X |
| 3,481,477 | 12/1969 | Farr | 23/259 X |
| 3,492,095 | 1/1970 | Tillem | 23/230 B |
| 3,496,777 | 2/1970 | Packer et al. | 73/425.4 R X |
| 3,554,700 | 1/1971 | Maxon | 23/259 X |
| 3,870,639 | 3/1975 | Moore et al. | 23/259 X |
| 3,955,423 | 5/1976 | Ohringer | 210/359 X |

*Primary Examiner*—Joseph Scovronek

*Attorney, Agent, or Firm*—Watson, Cole, Grindle & Watson

[57] ABSTRACT

Laboratory investigations in vitro of destruction and damage of living cells frequently involve labeling of the tissue cells in question with a radioactive isotope and subsequent dispersion of the cells in a suitable liquid. The dispersion is allowed to settle in a test tube, whereby a column of supernatant liquid is formed above precipitated cell particles. The radioactivity of said supernatant liquid is considered to be a measure of cell destruction and in order to measure the same while completely separated from the precipitated cell tissue, either the total amount or an accurately known fraction of the liquid must be collected, yet at the same time avoiding any collection of the precipitated particles. In order to secure this result, it is suggested according to the present invention that an actively absorbing surface of a liquid absorbent body be immersed into said amount of liquid in the container with a filter which is permeable to said liquid, but not to said particles, completely covering said surface. Said amount of liquid is allowed to be completely absorbed by the liquid absorbent body through said filter, which subsequently is separated from said actively absorbing surface before the absorbent body is removed from the container.

By utilizing an absorbent body with sufficient absorbing capacity to assure a complete inclusion of the supernatant liquid in said body, with the exclusion of all cell particles by means of said filter, the total leakage of radioactivity from the cells to the liquid may be measured with high reliability by means of a subsequent scintillation counting.

7 Claims, 2 Drawing Figures

PROCEDURE AND MEANS FOR COLLECTING LIQUID CONTAINING RADIOACTIVE TRACER ELEMENTS

The present invention concerns a procedure and means for collecting a liquid which contains radioactive trace elements from a container which also contains solid particles, particularly of biological tissue, while avoiding collecting such solid particles.

This kind of process is commonly used with laboratory investigations in vitro of destruction or death of living cells. Cells from biological tissue are initially labeled with a radioactive isotope and subsequently dispersed in a liquid with suitable properties for the purpose. This liquid will upon death of the labeled cells or damage to the cell membrane receive some of the radioactive isotope by leakage from within these cells. Then follows collection of the supernatant liquid formed above precipitated tissue particles, taking care that no cell tissue is included. The radioactivity of the separated supernatant liquid is then measured by known procedures, that is by scintillation counting.

Said collection of supernatant liquid prior to measuring its radioactivity is, according to known procedures, done by a pipette method which allows the removal of very precisely defined volumes of the liquid. However, it is not common practice always to observe corresponding precision as to the amount of liquid which is initially used for the dispersion of said tissue cells. This means that knowledge of the fraction of liquid which is removed by the pipette often is either inadequate or uncertain. Furthermore, there is no assurance that minor fragments of the cells are not sucked into the pipette together with the supenatant liquid. The entire procedure is, however, based upon the assumption that it is only the leakage of radioactivity into the supernatant liquid which is actually measured. For these reasons said known procedures may not always assure satisfactory accuracy and particularly not with routine evaluation of a great number of samples. Furthermore, in such case the same pipette is often used for several consecutive measurements, leaving some uncertainty with regard to accumulation of radioactivity in the pipette and related equipment.

It is, therefore, an object of the present invention to provide a procedure which overcomes the above disadvantages and allows reliable measurement of the radioactivity of the supernatant liquid with improved accuracy. To achieve this object according to the invention an actively absorbing surface of a liquid absorbent body is immersed into said amount of liquid in the container with a filter permeable to said liquid, but not to said particles, completely covering said surface, and said amount of liquid is allowed to be completely absorbed by the liquid absorbent body through said filter, which filter subsequently is separated from said actively absorbing surface before the absorbent body is removed from the container.

The invention, furthermore, concerns means for carrying out the above procedure, such means comprising according to the invention at least one liquid absorbent body adapted to be immersed in the amount of liquid in the container and thereby to present to said liquid an actively absorbing surface which is completely covered by a filter, said filter being permeable to said liquid, but impermeable to said particles and disposed to be separated from said actively absorbing surface subsequent to the complete absorption of the amount of liquid in said body through the filter, but before said body is removed from the container.

According to the invention, such means preferably comprise a plurality of liquid absorbent bodies mounted on a common base in a pattern corresponding to the same number of containers, e.g., test tubes, mounted in a frame, stand or similar structure, for the purpose of simultaneous collection of liquid from all said containers, each said liquid absorbent body being individually associated with a corresponding container. These bodies preferably are designed for single usage and are discarded upon evaluation of their radioactivity.

Figure 2:
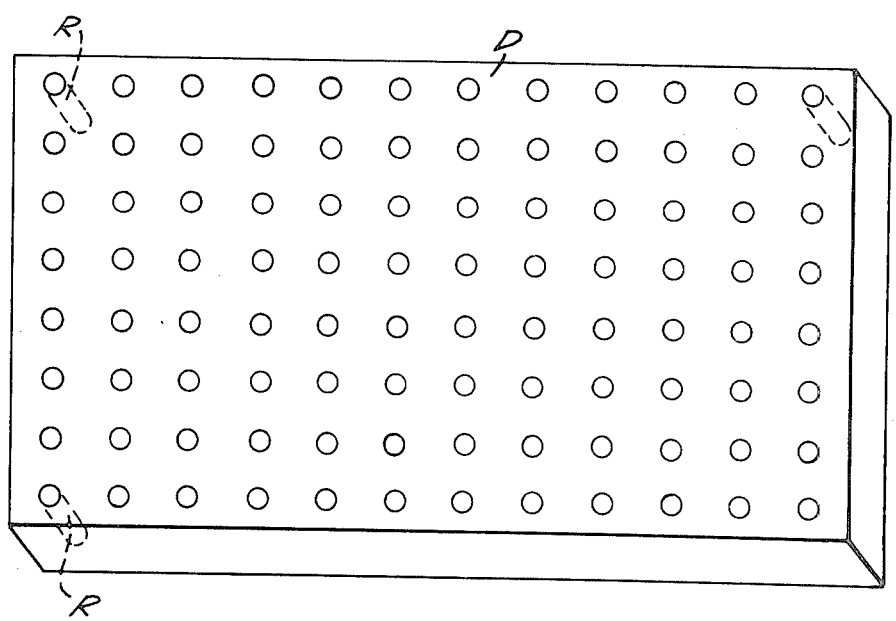

For a better comprehension of the special features and advantages of the present invention, a preferred embodiment will now be described with reference to the accompanying drawing, wherein:

FIG. 1 schematically shows a test tube containing a supernatant liquid and a certain amount of cell tissue, as well as a liquid absorbent body according to the invention, and FIG. 2 shows a frame designed for mounting a large number of test tubes for large-scale collection of samples according to the invention.

White corpuscles (lymphocytes) in the blood of two unrelated individuals A and B are separated from peripheral blood. One of these samples, e.g., sample A, is labeled with a radioactive isotope of chromium, Cr 57, and covered with a suitable antibody substance which will react with the cells from individual A. These radioactively labeled lymphocytes from individual A are next mixed with a large surplus of unlabeled lymphocytes from B. This mixture of cells is dispersed in a suitable liquid at 37° C for a few hours and allowed to precipitate. Due to the defensive features of the lymphocytes, some of the labeled cells from A will be destroyed and some radioactive chromium Cr 51 will leak into the supernatant liquid. This leakage will be a certain percentage of the Cr 51 originally present in the cells from individual A, and is a measure of the ability of lymphocytes from individual B to destroy the lymphocytes from individual A, as well as the activity of said anitbody with regard to cells from individual A. Thus, a measurement of the radioactivity of the entire supernatant liquid will serve as a basis for evaluating the action of antibodies in relation to certain patients.

Said mixing of cells with a suitable liquid is usually carried out in a suitable container, e.g., a test tube R, as indicated in FIG. 1. Gravity, in due time, concentrates all of the cells C at the bottom of the tube R, whereas the supernatant liquid S occupies the upper parts of the tube.

According to the invention a special, absorbent body L is employed for complete collection of the radioactive supernatant liquid. This body L consists of a liquid absorbing part A, the active surface of which is covered with a filter F, which is permeable to liquids, but not to particles. As shown in FIG. 1, the body is, in the present embodiment, shaped to conform to the cylindrical test tube R, for easy absorption and removal of the total amount of liquid S in the tube.

It will be understood that the active liquid absorbing surface of the body A is located preferably at one end only, and completely covered by a disk filter F, allowing only passage of liquid but not solid particles, thus effectively excluding all cells C from said liquid absorbing body A.

According to the invention, the absorption capacity of the body L is sufficient to secure easily the complete absorption of the amount of liquid S present in the tube R, whereupon the filter is separated from the body L while still in the tube, without any loss of liquid.

The body A is subsequently placed in a container suitable for mounting in a scintillation counter in order to determine the radioactivity of the absorbed supernatant liquid according to known methods. This may be done by scintillation counting of gamma radiation from the tracers present in the supernatant liquid contained in the liquid absorbent body A, this body preferably being composed of opaque materials, e.g., cotton, paper, etc.

Alternatively, the radioactivity may be determined by scintillation counting of beta radiation from said tracers in the absorbed supernatant liquid S, but in this case, the body A should consist of transparent materials, e.g., glass fibers, plastics, or the like, due to the low intensity of the beta radiation. A major advantage of the present procedure according to the invention is that the supernatant liquid S is completely absorbed in the body L, thus eliminating variations in initial liquid volume as a source of errors. Such errors often occur in the case of incomplete liquid transfer, which is the case with the methods and apparatus of the presently known state of the art.

Another advantage obtained by means of the present invention is the fact that the total amount of supernatant liquid S must pass through the filter F to be absorbed by the body A. As no cells C or parts thereof are able to penetrate said filter F, collection of pure supernatant liquid S in body A is assured, which strongly contributes to the reliability of the subsequent determination of radioactivity levels.

A further advantage of the present procedure and means according to the invention is the fact that the supernatant liquid may be collected from the test tube with negligible mechanical strain on the remaining cells, thus practically eliminating cell destruction and damage during collection.

The liquid absorbent body L is preferably made disposable and discarded after a single usage, in order to avoid accumulation of radioactivity which otherwise might be a health hazard as well as a source of error. Known procedures do not accomplish this, being based on suction of liquids through tubing, pipettes, etc.

According to an aspect of the present invention, several absorbent bodies may be handled simultaneously. A number of such bodies may be arranged according to a definite pattern on a common base, corresponding to the same number of containers, e.g., test tubes, mounted in a frame D, as indicated in FIG. 2. This arrangement allows simultaneous collection of liquid from each tube R by means of an individually associated body L. FIG. 2 shows 96 test tubes R mounted in a frame D in a rectangular pattern, so as to cooperate with 96 absorbing bodies mounted on a base in an identical pattern (not shown) thereby allowing for simultaneous penetration of each body L into an associated test tube R.

The above arrays of a large number of absorbing bodies and test tubes, respectively, greatly facilitates handling, storage and transportation of the active bodies during the actual absorption process as well as afterwards. The filter F may be bonded to the body L by means of a bonding agent, which is liable to be dissolved under the influence of the liquid present in the tube R to secure an easy separation of the filter from the liquid absorbent body subsequent to the complete absorption of said liquid. Said bonding may, however, also be broken by mechanical means.

We claim:

1. A method for collecting a given amount of liquid containing radioactive tracer elements from a container which also contains solid particles, in particular biological tissue, without at the same time collecting such particles, comprising the steps of immersing an actively absorbing surface of a liquid absorbent body in said amount of liquid, said surface covered with a filter permeable to said liquid, but not to said particles, completely absorbing said amount of liquid in the liquid absorbent body through said filter, subseqently separating said filter from said actively absorbing surface, and removing the absorbent body from the container after separation of the filter.

2. A method according to claim 1, wherein the separation of said filter from said surface is accomplished by dissolution with said liquid.

3. A method according to claim 1, wherein the separation of said filter from said surface is accomplished by mechanically breaking said filter from said surface.

4. Apparatus for collecting a given amount of liquid containing radioactive tracer elements from a container which also contains solid particles, in particular biological tissue, without at the same time collecting such particles, comprising at least one liquid absorbent body adapted to be immersed in the amount of liquid in the container and having thereon an actively absorbing surface disposed so as to contact said amount of liquid, a filter completely covering said actively absorbing surface, said filter being permeable to said liquid, but impermeable to said particles, and bonding means attaching said filter to said actively absorbing surface, said bonding means being liable to be dissolved under the influence of the liquid present in the container so as to allow separation of said filter from said actively absorbing surface subsequent to the complete absorption of the amount of liquid by said body through the filter, but before said body is removed from the container.

5. Apparatus according to claim 4, wherein said absorbent body is comprised of opaque materials so as to be adapted to scintillation counting of gamma radiation from said tracer elements in the absorbed liquid.

6. Apparatus according to claim 4, wherein said absorbent body is comprised of transparent materials so as to be adapted to scintillation counting of beta radiation from said tracer elements in said absorbed liquid.

7. Apparatus according to claim 4, wherein a plurality of absorbent bodies are mounted on a common base in a pattern corresponding to a like number of containers mounted in a frame to allow simultaneous collection of liquid from each of the containers by means of an associated one of said bodies.

* * * * *